United States Patent [19]

Lander et al.

[11] Patent Number: 5,236,152
[45] Date of Patent: Aug. 17, 1993

[54] COOLING/FUEL SYSTEM FOR HYPERSONIC FLIGHT

[75] Inventors: Herbert R. Lander, Westlake Village; Robert E. Schnurstein, Northridge, both of Calif.

[73] Assignee: Rockwell International Corporation, Seal Beach, Calif.

[21] Appl. No.: 828,381

[22] Filed: Jan. 30, 1992

[51] Int. Cl.$^5$ .............................................. B64D 37/34
[52] U.S. Cl. .......................... 244/117 A; 244/135 R; 431/2; 60/206
[58] Field of Search ................ 244/53 R, 73, 74 R, 244/117 A, 135 R; 60/206, 207; 62/4; 431/2

[56] References Cited

U.S. PATENT DOCUMENTS

| | | | |
|---|---|---|---|
| 3,067,594 | 12/1962 | Bland et al. | 62/4 |
| 3,173,247 | 3/1965 | Smith et al. | 60/206 |
| 3,263,414 | 8/1966 | Herbst | 60/206 |
| 4,817,890 | 4/1989 | Coffinberry | 244/135 R |
| 4,919,364 | 4/1990 | Helmut et al. | 244/55 |
| 4,934,632 | 6/1990 | Kyusik et al. | 244/53 |

OTHER PUBLICATIONS

Article entitled "Parametric Study of Airframe-Integrated Scramjet Cooling Requirement," Journal of Propulsion and Power, Authors: Takeshi Kanda, Goro Masuya, Yoshio Wakamatsu, Nobuo Chinzei, and Akio Kanmuri, vol. 7, No. 3, May–Jun. 1991, pp. 431–436.
Article entitled "Active Cooling of a Hydrogen–Fueled Scramjet Engine," Journal of Aircraft, Authors: L. L. Pagel and W. R. Warmbold, vol. 6, No. 5, Sep.–Oct. 1969, pp. 472–474.
Article entitled "Mach 2 Combustion Characteristics of Hydrogen–Hydrocarbon Fuel Mixtures," Johns Hopkins University, The 24th JANNAF Combustion Meeting, vol. 2, pp. 155–169.

*Primary Examiner*—Galen Barefoot
*Attorney, Agent, or Firm*—H. Fredrick Hamann; Harry B. Field; David G. Faulkner

[57] ABSTRACT

The present invention provides for the integration of structural cooling and fuel treatment within hypersonic vehicles. This is achieved by channeling a hydrocarbon fuel to a portion of the aircraft structure and imparting via the heat sink effect sufficient heat to cause a pyrolysis of the hydrocarbon fuel. After pyrolysis, the resulting fractions are then utilized as a fuel by the vehicle.

3 Claims, No Drawings

COOLING/FUEL SYSTEM FOR HYPERSONIC FLIGHT

BACKGROUND AND SUMMARY OF THE INVENTION

The invention relates to a method for simultaneously (1) cooling select surfaces of a hypersonic vehicle and (2) providing fuel as an energy source for consumption by a ramjet engine or the like in hypersonic vehicles.

At present, efforts have been undertaken to develop hypersonic vehicles capable of launching and reaching cruising speeds of several Mach.

Such hypersonic vehicles are, of course, subject to extreme temperature fluctuations within the vehicle's envelope of performance. Specifically, the leading edges of such vehicle frames as well as the internal construction associated with engines necessary to power the vehicle require that design parameters incorporate means for insuring structural survivability during hostile operating parameters.

Furthermore, consideration must be given to not only thermal environment requirements concerning the internal engine(s) but also to the fuel of choice which must realize a high heat of combustion while maintaining good cooling characteristics.

It is, therefore, an object of the present invention to provide a means for efficient structural cooling not only of the vehicle but also of the propulsion elements attendant thereto.

According to the invention, this object is achieved by means of an arrangement, whereby the fuel system is designed to allow the flow of fuel via fuel system conduits such that the fuel is caused to pass adjacent to areas of high thermal flux in hypersonic vehicle operation. Examples of such vehicle design and function are set forth in U.S. Pat. Nos. 4,919,364 (Apr. 24, 1990) and 4,934,632 (Jun. 19, 1990), both incorporated herein by reference.

Naturally, the propulsion system provides means known to those skilled in the art for conveying the fuel which has been heated by association with high temperature areas of the vehicle structure and directing such heated fuel to the combustion chamber of the vehicle engine.

In furtherance of the objective of the present invention, a select hydrocarbon fuel is utilized such that heat input to the fuel is used to thermally crack the fuel, cooling the structure through the endothermic pyrolysis reaction and forming reactive olefinic fuel fractions which are then injected into the high velocity internal flow stream of the vehicle propulsion system.

DETAILED DESCRIPTION OF THE INVENTION

Further to the summary of the invention provided above, the instant invention allows for a method of simultaneous heat sink and reactive fuel fraction production from hydrocarbons useful in hypersonic propulsion applications.

The method is achieved by providing:

(i) a hypersonic vehicle having high heat flux regions wherein a hydrocarbon fuel is exposed to high temperature regions of the vehicle structure thereby imparting a temperature increase to the hydrocarbon fuel such that the hydrocarbon pyrolyzes into olefinic fractions;

(ii) reducing temperature gradients of vehicle structural components and directly of the high heat flux area thereof by heat transfer from the high heat flux region to the hydrocarbon fuel; and (iii) then utilizing the olefinic fractions as a fuel in the hypersonic propulsion of hypersonic vehicles and the like.

The preferred hydrocarbon fuels which may be utilized are saturated aliphatic hydrocarbons, normally from $C_6$ to $C_{40}$ such as hexane, heptane, octane, etc. These hydrocarbon fuels have an average molecular weight of between 100 and 1,000 and during the pyrolysis process, the hydrocarbon temperature is generally increased from 10° C. to 1000° C. Although the invention has been described hereinabove, it is to be clearly understood that the same is by way of illustration and example, and is not to be taken by way of limitation. The spirit and scope of the present invention are to be limited only by the terms of the appended claims.

What is claimed:

1. A method of simultaneously heat sink and reactive fuel factions production from hydrocarbons having an average molecular weight of between 100 and 1,000 in hypersonic propulsion applications comprising:

(i) in a hypersonic vehicle having high heat flux structural regions, causing a hydrocarbon exposure to a high heat flux structural region and imparting a temperature increase to the hydrocarbon;

(ii) reducing temperature gradients of the high heat flux structural region by heat transfer from said high flux structural region to the hydrocarbon such that a portion of the hydrocarbon pyrolyzes into olefinic fractions; and (iii) utilizing the olefinic fractions as a fuel in hypersonic propulsion in a hypersonic vehicle.

2. The method of claim 1 wherein said hydrocarbon is selected from aliphatics of $C_6$ to $C_{40}$.

3. The method of claim 1 wherein the hydrocarbon temperature is increased from 10° C. to 1000° C.

* * * * *